United States Patent [19]

Chen

[11] Patent Number: 4,929,234
[45] Date of Patent: May 29, 1990

[54] AUTOMATIC DRIP INFUSION SET

[76] Inventor: A-Ten Chen, 6, Lane 71, Min Hsing St., Taichung, Taiwan

[21] Appl. No.: 330,643

[22] Filed: Mar. 30, 1989

[51] Int. Cl.⁵ .............................................. A61M 5/00
[52] U.S. Cl. .................................. 604/132; 604/154; 604/224; 222/226
[58] Field of Search .................. 604/151, 153–155, 604/131, 138, 209, 218, 224; 222/95, 214, 326, 333

[56] References Cited

U.S. PATENT DOCUMENTS

| | | | |
|---|---|---|---|
| 4,457,752 | 7/1984 | Vadasz | 604/153 |
| 4,634,430 | 1/1987 | Polaschegg | 604/153 |
| 4,676,122 | 6/1987 | Szaso et al. | 222/333 |

Primary Examiner—Stephen C. Pellegrino
Attorney, Agent, or Firm—Bacon & Thomas

[57] ABSTRACT

This invention relates to an automatic drip infusion set which is applicable for use in a situation of low atmospheric pressure, not to be suspended from a higher place during application, and which can provide alarm signal accordingly. The device includes a motor to drive an extension rack assembly by means of a speed variator so as to let the push plate which is connected with the rack assembly at the front end compress a compressible drip bottle to infuse the solution contained therein into patient's body smoothly. During moving of the rack assembly, it will trigger a buzzer and a stop control switch respectively so as to stop infusion process and give an audio alarm signal when the solution of the drip bottle is about exhausted.

3 Claims, 3 Drawing Sheets

AUTOMATIC DRIP INFUSION SET

BACKGROUND OF THE INVENTION

The present invention is to provide an easy-to-carry drip infusion set which will automatically stop drip infusion and give an audio alarm when the solution contained in the drip bottle is going to be exhausted, and which uses a motor to drive a driving gear wheel to rotate so as to further drive an extension rack assembly to move forward to compress a compressible drip bottle by means of a push plate connected with the rack assembly at the front end such that a constant and quantitative drip infusion process is achieved.

Regular drip infusion is performed by suspending a drip bottle from a drip stand such that the difference of elevation will allow the solution contained in the drip bottle be forced to drip into patient's body through blood circulation. In this process, following inconveniences and risks may be encountered:

(1) Because drip infusion process takes a lot of time to complete, the patient tends to be sleeping to become unaware of the danger of exhaustion of the infusion solution, and the patient's blood may be easy to adversely flow out through the needle.

(2) During long time drip infusion process, polyuric condition may happen to the patient. It is very embarrassing to the patient how to move the drip stand into the toilet or how to carry the drip bottle with one hand and fix the needle with the other hand while going to discharge.

(3) Because the drip infusion is performed by means of the difference of elevation, an air vent must be inserted into the drip bottle to let the internal space of the drip bottle be communicated with the atmosphere so as to allow atmospheric pressure force the infusion solution to drip into patient's body. In consequence, the microbes which are floating in the air may get into the drip bottle to cause contamination and to threaten the weak patient.

(4) Because the drip bottle must be suspended from a higher place during drip infusion process, the process will become more difficult to perform under some special conditions (for example, for performing first-aids on a traffic accident or any accident happens in the mountain).

DETAILED DESCRIPTION OF THE PREFERRED EMBODIMENTS

Figure 1:
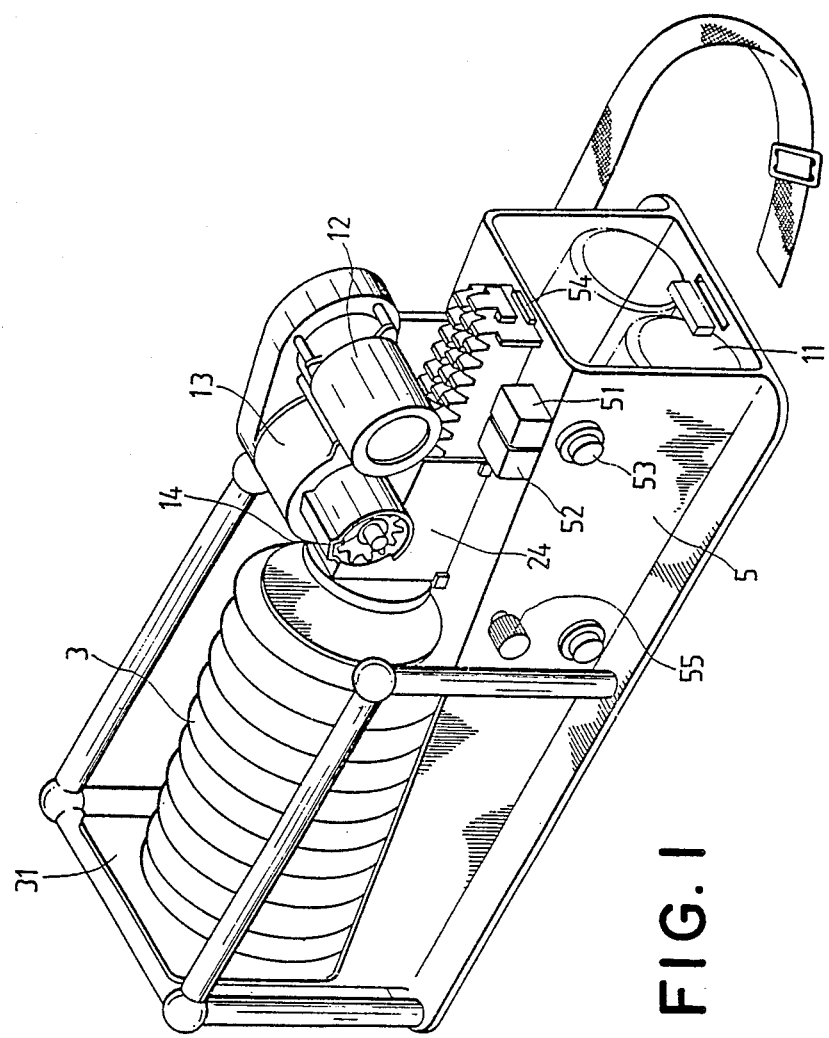
FIG. 1 is a perspective view of an automatic drip infusion set embodying the present invention.

Referring to the annexed drawings, an automatic drip infusion set includes a driving mechanism (1), which is comprised of a rechargeable battery (11), a motor (12), a speed variator (13), and a driving gear wheel (14), and a compression mechanism (2), which is comprised of a rack holder (24) for sliding therein of a rack assembly, a rack assembly comprised of a main rack (23) and an auxiliary rack (22), and a push plate (21).

Figure 2:
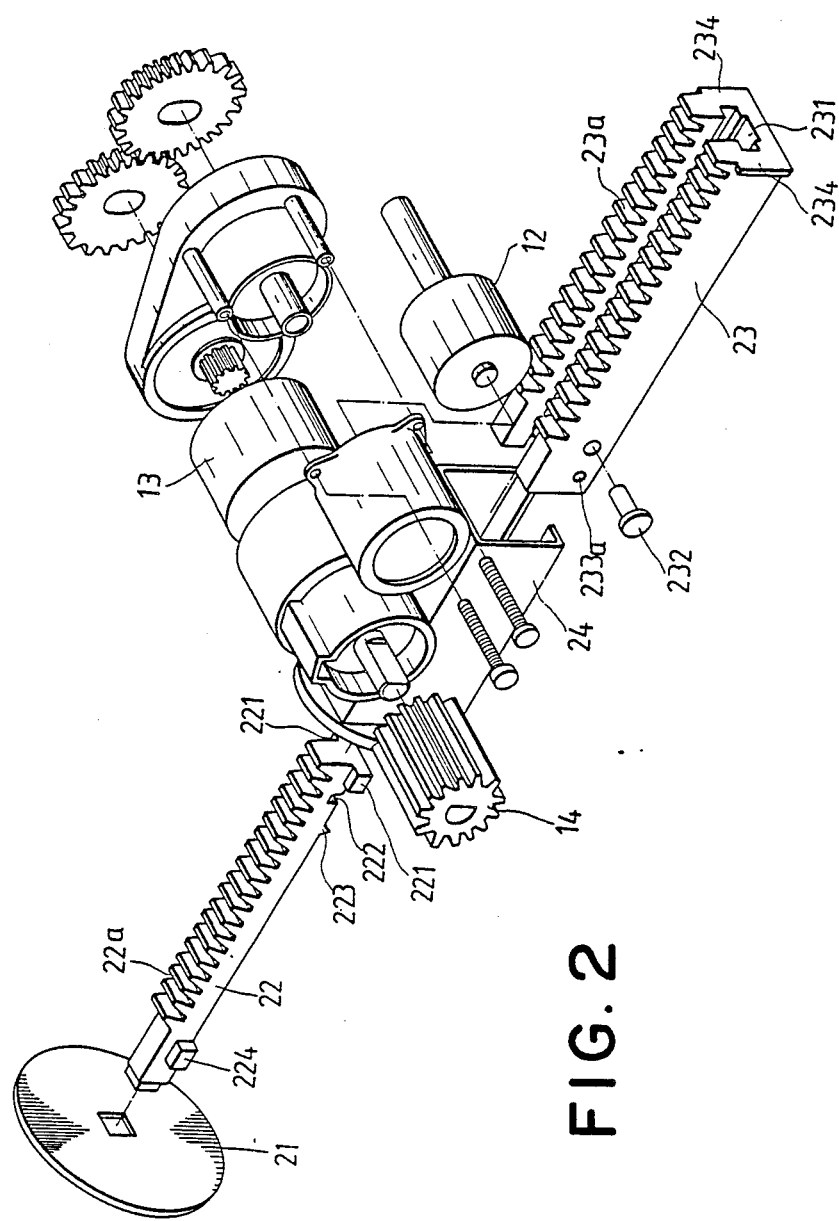
FIG. 2 is a fragmentary structural view of the said embodiment of the present invention.
Figure 3:
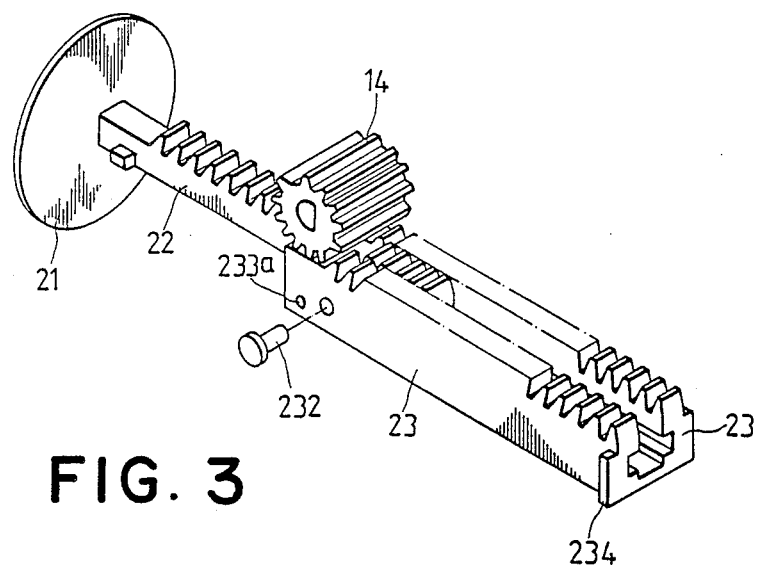
FIG. 3 is a perspective view of the main and auxiliary rack assembly.

The compression mechanism (2) is specially designed to become expansible, so as to minimize space consumption and to permit for easy transportation, wherein the main rack (23) is set to slide in the [ ] shaped rack holder (24), comprising a toothed portion (23a) made at the top and arranged in a length shorter than the total length of the main rack (23), and a flat top end (as shown in FIG. 2) made at the front of the toothed portion (23a); and the auxiliary rack (22) which includes a toothed portion (22a) at the top is set to slide along the [ ] shaped slide way (231) of the main rack (23), and connected with the push plate (21) at the front to compress a drip bottle (3), and wherein the toothed portions (23a) and (22a) of the main and auxiliary racks (23) and (@2) are arranged to engage with the driving gear wheel (14) respectively.

When the driving gear wheel (14) is driven to rotate by the motor (12) through the speed variator (13), it will carry the auxiliary rack (22) to move forward slowly to let the front push plate (21) push a compressible bottle (3) against a check plate (31). In order to minimize the size for easy carriage, the length of the auxiliary rack (22) is just about half size of the compressible drip bottle (3). However, the auxiliary rack (22) is movably connected with the main rack (23). The auxiliary rack (22) includes a tenon (221) bilaterally made at the rear end. The main rack (23) is having a stop pin (232) pivotally penetrated through one lateral side to slightly project into the slide way (231) without interfering with the sliding of the auxiliary rack (22) along the slide way (231). Therefore, as soon as the auxiliary rack (22) is driven by the driving gear wheel (14) to move forward to its maximum extent, the side tenon (221) of the auxiliary rack (22) will be stopped by the stop pin (232) which projects into the sliding way (231) and, the main rack (23) will be carried to move forward to let the toothed portion (23a) be engaged with the driving gear wheel (14). When the driving gear wheel (14) is continuously driven to rotate, it will break away from the auxiliary rack (22) to fully engage with the main rack (23) so as to drive the main rack (23) to move forward.

Figure 4:
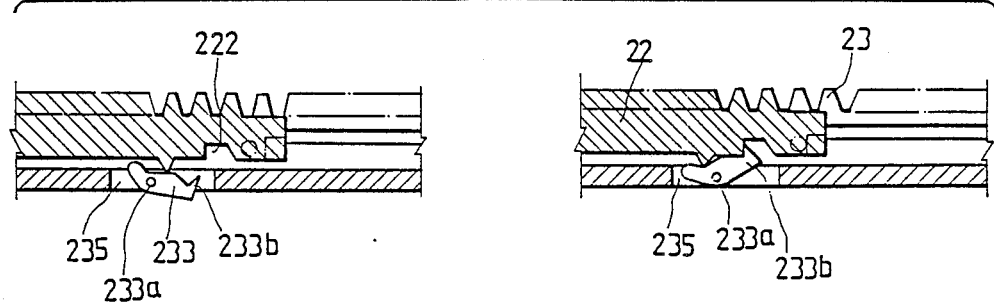
FIG. 4 are elevated sectional view drawings of the main and auxiliary rack assembly, illustrating the retaining motion of the pawl.

Because the push plate (21) which is driven to compress the compressible drip bottle (3) is connected with the auxiliary rack (22) at the front, when the auxiliary rack (22) is released from the engaged position with the driving gear, the push force may also be stopped concomitantly to become unable to compress the compressible drip bottle (3). In order to solve this problem, the auxiliary rack (22) is arranged to provide a push block (223) protrudently made at the bottom, and a retaining groove (222) made at the bottom between the retaining groove (222) and the side tenon (221). When the side tenon (221) is stopped by the stop pin (232) in the slide way (231), the push block (223) will simultaneously push the front end of a shift pawl (233), which is revolvably mounted on a pivot pin (233a) in an opening (235) inside the slide way (231) of the main rack (23), to let the hook end (233b) of the shift pawl (233) be lifted to engage with the retaining groove (222) of the auxiliary rack (22), such that the auxiliary rack (22) is constrained by the pawl (233) and pushed to continuously move forward by the main rack (23) (as shown in FIG. 4).

In addition to the extension rack assembly, another feature of the present invention is the alarm and automatic stop mechanism. The main rack (23) is having a stop plate (234) bilaterally made at the rear end at both sides. When the toothed portion (23a) is driven by the driving gear wheel (14) to move to its limit of engagement (that is, the compressible drip bottle (3) is about to be compressed to the limit), the stop plate (234) will firstly trigger a micro-switch (51), which is mounted on the housing (5), to turn on a buzzer (not shown) to give an audio alarm signal, and then trigger another micro-switch (52) to turn off the motor (12).

When the drip bottle (3) is used up and replacement is required, the motor shall be turned on, by means of the control of a control switch (53) which is mounted on the housing (5), to rotate counter-clockwise so as to let the driving gear wheel (14) drive the main rack (23) to retreat and to further drive the auxiliary rack (22) to retreat concomitantly, by means of the the retaining effect of the stop pin (232) of the main rack (23) with the tenon (221) of the auxiliary rack (22). As soon as the main rack (23) is retreated to let the toothed portion (23a) be released from the engaged condition with the driving gear wheel (14), and before running over the flat front top end of the main rack (23), the driving gear wheel (14) will become in engagement with the toothed portion (22a) of the auxiliary rack (22) to keep driving the auxiliary to move backward and, at the same time, the bottom push block (223) of the auxiliary rack (22) will push the rear end of the pawl (233) to let the hook end (233b) break away from the retaining groove (222) so as to permit the auxiliary rack (22) be smoothly driven to slide backward into the slide way (231).

In order to prevent the main and auxiliary racks (23) and (22) from breaking away from the rack holder (24) while retreating, a stop block (54) is made at the rear top end of the housing (5) to limit the backward movement of the main and auxiliary racks (23) and (22). The auxiliary rack (22) also comprises two stop tenons (224) bilaterally disposed at the front end. Therefore, when the auxiliary rack (22) is retreated to its limit, the tenons (224) will be stopped by the stop pin (232) of the main rack (23) to confine the backward movement of the auxiliary rack (22) within a suitable range.

In order to accelerate the retreating speed of the compression mechanism (2) to minimize time consumption during the process, a control knob (55) is made on the housing (5) to regulate the revolving speed of the motor so as to further control the forwarding as well as the retreating speed of the main and auxiliary racks (23) and (22). Therefore, the infusion speed of the compressible drip bottle (3) can be adjusted.

In another preferred embodiment, a power connector which is connected to the buzzer control micro-switch (51) at one end, and is received in the housing (5) is provided for connection to the interphone or alarming equipment in a hospital room to call the nurses' station or to let the alarm lamp in the nurses' station be turned on when the infusion of the compressible drip bottle (3) is going to be exhausted and the buzzer of the present invention is turned on to buzz.

In conclusion, the present invention is to provide such an automatic drip infusion set having five main advantages as hereunder:

(1) The present invention is motorized, and the infusion speed may be adjusted according to requirement. Therefore, a constant and most suitable infusion speed can be obtained in the most accurate and simple way without through visual check as in the conventional dip infusion set.

(2) Because the present invention gives a compulsory infusion by means of self-provided motive power, the dip infusion set of the present invention needs not to be suspended from a higher place, and therefore, it can be movably placed at any place, for example, beneath the bed or on a desk.

(3) Because the present invention uses a small motor and small speed variator and the power is supplied by means of rechargeable battery, the drip infusion set of the present invention is very convenient to transport and very practical for use in rude terrains, such as for use in first-aid in mountaineering accident or in an emergency.

(4) Because the present invention adopts an extension rack design to minimize space consumption, when a handle or belt is attached, the whole drip infusion set may be carried with the patient to move to anywhere.

(5) Because the present invention adopts compulsory infusion process, the infusion will not be interfered with the atmospheric pressure. Even in the zero gravity space, the present invention can still be well performed.

I claim:

1. An automatic drip infusion set, including
   a compressible drip bottle to be compressed by a push plate to let the solution contained therein be infused into patient's body;
   a rack holder to receive a main rack and an auxiliary rack and to let the main rack be sliding therein, having a driving gear wheel mounted thereon at the top to drive the main and the auxiliary racks to move;
   a main rack movably set in the rack holder, having a toothed portion made thereon at the top, said toothed portion being arranged in a length smaller than the length of the main rack so as to confine a flat front top end, a slide way made therein at the middle portion for sliding thereon of a small rack, a stop pin pivotally made at one side to slightly project into the slide way;
   an auxiliary rack movably set in the slide way of the main rack, having a toothed portion made at the top, and a push plate connected at the front end; and
   a driving gear wheel mounted in the rack holder at an upper position to engage with the toothed portions of the main rack and the auxiliary rack, being driven by a motor through a speed variator to drive the main rack and the auxiliary rack to move forward or backward;

characterized in that the rotation of the driving gear drives the auxiliary rack to move forward to further let the tenon which is made at the rear end of the auxiliary rack be retained with the stop pin of the main rack so as to carry the main rack to move forward and to let the toothed portion of the main rack be engaged with the driving gear wheel.

2. The automatic drip infusion set as set forth in claim 1, wherein said auxiliary rack is arranged to provide a push block protrudently made at the bottom, and a retaining groove made at the bottom between said retaining groove and the said tenon which is made at the rear end; said main rack having an opening made at the front end and a shift pawl revolvably mounted on a pivot pin in said opening, and wherein said push block pushes the front end of said shift pawl to let the rear hook end of said shift pawl be lifted to engage with said retaining groove, when the rear end of said auxiliary rack is driven to move toward the front end of said main rack, such that said main rack will be driven to let said shift pawl push said auxiliary rack to concomitantly move forward.

3. The automatic drip infusion set as set forth in claim 1, wherein said auxiliary rack is comprising a stop tenon made at the front end and another tenon made at the rear end to respectively be constrained by the said stop pin of said main rack during forward or backward movement so as to prevent from breaking away from the main rack.

* * * * *

UNITED STATES PATENT AND TRADEMARK OFFICE
CERTIFICATE OF CORRECTION

PATENT NO. : 4,929,234

DATED : May 29, 1990

INVENTOR(S) : A-Tien Chen

It is certified that error appears in the above-identified patent and that said Letters Patent is hereby corrected as shown below:

On the title page, item [76]:

Please correct the Inventor's Name as follows:

Delete "A-Ten Chen", and insert therefor:

-- A-Tien Chen --.

Signed and Sealed this

Twenty-third Day of July, 1991

*Attest:*

HARRY F. MANBECK, JR.

*Attesting Officer*  *Commissioner of Patents and Trademarks*